United States Patent [19]

Sumanaweera et al.

[11] Patent Number: 5,351,006
[45] Date of Patent: Sep. 27, 1994

[54] METHOD AND APPARATUS FOR CORRECTING SPATIAL DISTORTION IN MAGNETIC RESONANCE IMAGES DUE TO MAGNETIC FIELD INHOMOGENEITY INCLUDING INHOMOGENEITY DUE TO SUSCEPTIBILITY VARIATIONS

[75] Inventors: Thilaka S. Sumanaweera, Palo Alto; Gary H. Glover, Menlo Park; John R. Adler, Stanford, all of Calif.

[73] Assignee: Board of Trustees of the Leland Stanford Junior University, Stanford, Calif.

[21] Appl. No.: 135,143

[22] Filed: Oct. 12, 1993

Related U.S. Application Data

[63] Continuation of Ser. No. 834,178, Feb. 7, 1992, abandoned.

[51] Int. Cl.$^5$ ............................................. G01V 3/00
[52] U.S. Cl. .................................... 324/309; 324/307
[58] Field of Search ............... 324/300, 307, 309, 312, 324/313, 318

[56] References Cited

U.S. PATENT DOCUMENTS 4,823,085  4/1989  Fuderer et al. ...................... 324/309
4,876,509  10/1989  Perlmutter .......................... 324/309

OTHER PUBLICATIONS

"Geometrical Image Transformation to Compensate for MRI Distortions" by Chang et al. SPIE vol. 1233 Med. Imaging IV (1990) (month of pub. unknown).
"Total Inhomogeneity Correction Including Chem. Shifts and Susceptibility by View Angle Tilting" Med. Physics vol. 15 No. 1 Jan. 1988, Cho, Z. H. et al.
"MR Susceptibility Distortion Quantification and Correction for Steroetaoxy" by Sunumaweera et al. Proc. SPIE/SPSE Feb. 9-14, 1992.

*Primary Examiner*—Louis Arana
*Attorney, Agent, or Firm*—Townsend and Townsend Khourie and Crew

[57] ABSTRACT

An in-vivo correction method for the non-linear, shape dependent spatial distortion in MR images due to magnetic field inhomogeneity including inhomogeneity due to susceptibility variations is disclosed. Geometric distortion at the air/tissue and tissue/bone interfaces before and after the correction is quantified using a phantom. The results are also compared to the "distortion-free" CT images of the same phantom. Magnetic susceptibility of cortical cattle bone was measured using a SQUID magnetometer and found to be −8.86 ppm which is quite similar to that of tissue (−9 ppm). The distortion at the bone/tissue boundary was negligible while that at the air/tissue boundary created displacements of about 2.0 mm with a1.5T main magnetic field and a 3.13 mT/m gradient field, a significant value if MR images are used to localize targets with the high accuracy expected for stereotaxic surgery. The correction method reduces the errors to at least the same level of accuracy as CT.

10 Claims, 8 Drawing Sheets

METHOD AND APPARATUS FOR CORRECTING SPATIAL DISTORTION IN MAGNETIC RESONANCE IMAGES DUE TO MAGNETIC FIELD INHOMOGENEITY INCLUDING INHOMOGENEITY DUE TO SUSCEPTIBILITY VARIATIONS

This is a continuation of application Ser. No. 07/834,178, filed Feb. 7, 1992, now abandoned.

BACKGROUND OF THE INVENTION

This invention relates generally to magnetic resonance imaging (MRI), and more particularly the invention relates to the correction of spatial distortion in magnetic resonance images due to magnetic susceptibility variations in an object being imaged.

Magnetic resonance imaging (MRI), is a non-destructive method for the analysis of materials and represents a new approach to medical imaging. It is generally non-invasive and does not involve ionizing radiation. In very general terms, nuclear magnetic moments are excited at specific spin precession frequencies which are proportional to the local magnetic field. The radio-frequency signals resulting from the precession of these spins are received using pickup coils. By manipulating the magnetic fields, an array of signals is provided representing different regions of the volume. These are combined to produce a volumetric image of the nuclear spin density of the body.

The term "stereotaxis" refers to a collection of neurosurgical techniques that apply simple geometric relationships to radiological studies thereby facilitating the treatment of certain disorders of the brain with great accuracy. Over the past decade computed tomography (CT) has been the primary mode of target localization in stereotaxic surgery. However with the advent of the high resolution, high SNR, fast MR scanners, MR is more frequently applied to stereotaxic surgery because of its superior soft-tissue contrast.

Although Magnetic Resonance Imaging has proved to be useful in diagnostic radiology, it has yet to prove its utility in therapy for two major reasons. First, the geometric distortion associated with MR registration is quite significant. Second, present MR techniques are excellent in imaging soft-tissue and fat regions; but fail to image bony areas. In planning some surgical cases, the lack of bony detail in MR images is a disadvantage. Thus CT and MR provide useful information complementary to each other. As a result, there have been many attempts to combine the two modalities. Most efforts in multimodal image merging including MR have ignored the geometric distortion inherent to MR.

Misregistration due to magnetic susceptibility differences is by far the most complex source of error. It is dependent on both the material present in the imaging volume and the shapes of the structures being imaged. Usually such structures consist of inhomogeneous and anisotropic material. Although there have been recent attempts to characterize the fields inside the head by finite element analysis of Maxwell's equations, in general it is difficult to predict the amount of distortion accurately using such schemes. The magnetic properties of the human body are difficult to estimate and vary considerably depending on the factors such as the water content. Cho et al., "The Total Inhomogeneity Correction Including Chemical Shift and Susceptibility by View Angle Tilting," *Medical Physics*, Vol. 15, Jan.-/Feb. 1988, have proposed a clever method to correct the susceptibility distortion using view angle tilting by adding a compensation gradient. In practice however, difficulties arise due to bandwidth limitations of the gradient amplifiers. In addition, Chang and Fitzpatrick, "Geometric Image Transformation to Compensate for MRI Distortions," *SPIE Medical Imaging: Image Processing*, Vol. 1233, pp. 116–127, 1990, have presented a differential equation approach to correction of MR distortion with the assumption of $C°$ continuity in the image profile.

SUMMARY OF THE INVENTION

The present invention is directed to an improved method and apparatus for correcting spatial distortion in magnetic resonance images due to magnetic susceptibility variations in an object being imaged.

The method is practiced in vivo by establishing a map of the magnetic field, $B_o$, at various points in an object to be imaged, thereby defining the geometric distortion due to magnetic susceptibility variations at the various points. The $B_o$ map is obtained by applying different magnetic pulse sequences from which a measure of the magnetic susceptibility effects can be obtained. For example, gradient recalled echo (GRE) sequences or spin echo sequences can be applied so that the phase difference in two acquisitions gives a measure of the magnetic susceptibility at each point.

Geometric distortion at air/tissue interfaces in a phantom before and after correction in MR images are compared to distortion free CT images of the phantom. The invention reduces the magnetic susceptibility errors to the same level of accuracy as CT.

The invention and objects and features thereof will be more readily apparent from the following detailed description and appended claims when taken with the drawings.

DETAILED DESCRIPTION OF THE ILLUSTRATIVE EMBODIMENTS

Figure 1A:
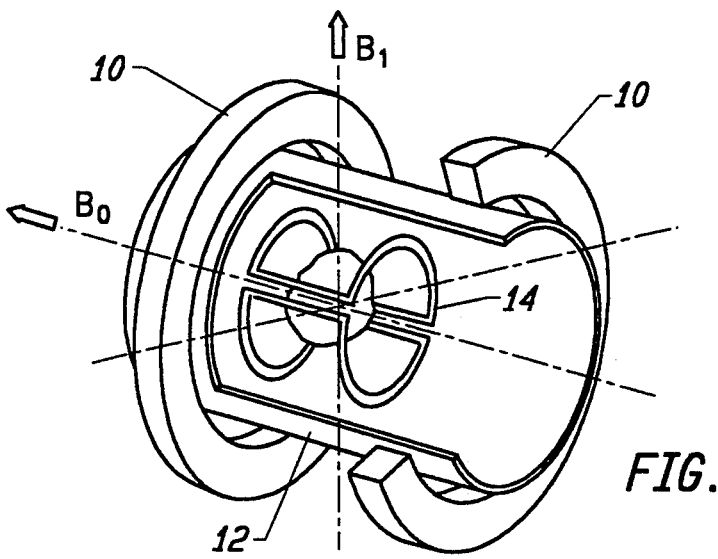
FIGS. 1A–1D illustrate the arrangement of conventional MRI apparatus and magnetic fields generated therein.
Figures 1B, 1C, 1D:
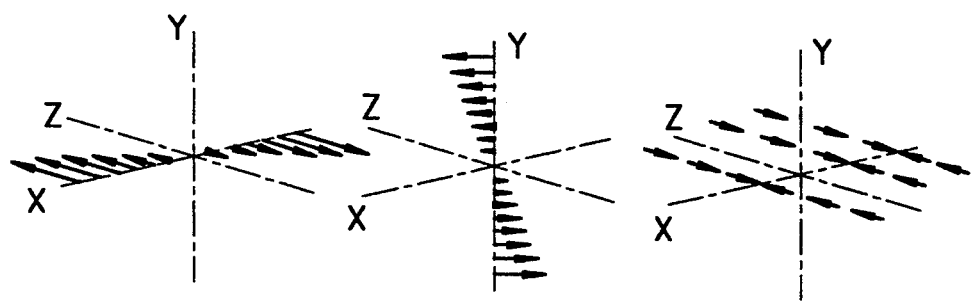

Referring now to the drawings, FIG. 1A is a perspective view partially in section illustrating coil apparatus in an NMR imaging system, and FIGS. 1B–1D illustrate field gradients which can be produced in the apparatus of FIG. 1A. This apparatus is discussed by Hinshaw and Lent, "An Introduction to NMR Imaging: From the Bloch Equation to the Imaging Equation," *Proceedings of the IEEE*, Vol. 71, No. 3, March 1983, pp. 338–350. Briefly, the uniform static field $B_o$ is generated by the magnet comprising the coil pair 10. A gradient field $G_x$ is generated by a complex gradient coil set which can be wound on the cylinder 12. An RF field $B_I$ is generated by a saddle coil 14. A patient undergoing imaging would be positioned along the Z axis within the saddle coil 14.

In FIG. 1B an X gradient field is shown which is parallel to the static field $B_o$ and varies linearly with distance along the X axis but does not vary with distance along the Y and Z axes. FIGS. 1C and 1D are similar representations of the Y gradient and Z gradient fields, respectively.

Figure 2:
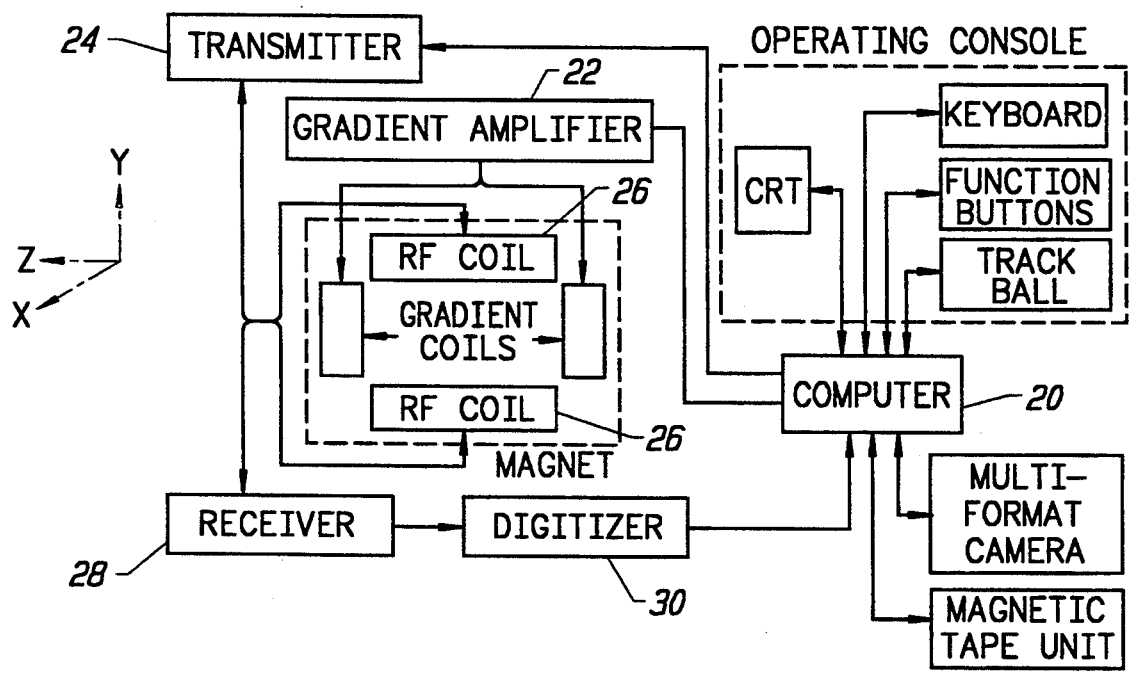
FIG. 2 is a functional block diagram of MRI imaging apparatus.

FIG. 2 is a functional block diagram of the imaging apparatus as disclosed in *NMR-A Perspective on Imaging*, General Electric Company, 1982. A computer 20 is programmed to control the operation of the NMR apparatus and process FID signals detected therefrom. The gradient field is energized by a gradient amplifier 22, and the RF coils for impressing an RF magnetic moment at the Larmor frequency is controlled by the transmitter 24 and the RF coils 26. After the selected nuclei have been flipped, the RF coils 26 are employed to detect the FID signal which is passed to the receiver 28 and thence through digitizer 30 for processing by computer 20.

Ideally, during an MR scan a constant magnetic field is expected everywhere in the imaging body. Due to diamagnetic and paramagnetic susceptibility variations in various parts inside the object, we get slight variations of the $B_o$ field given by:

$$\hat{B}_o = (1 + \chi) B_o$$

where $\chi$ is the magnetic susceptibility. The effect of this magnetic field variation on MR images is three fold:

1. During the slice selection phase, we may get non-planar, irregularly shaped slices.
2. Geometric distortions that depend on the object shape appear in the image plane.
3. Erroneous pixel intensity variations occur concomitantly with the effect 2 above.

Susceptibility misregistration is prevalent in both Gradient-Recalled Echo (GRE) and Spin Echo (SE) sequences especially if the echo time $T_E$ is large, the gradient field $G_z$ is small and $B_o$ is large.

Lüdeke et al., "Susceptibility Artifacts in NMR Imaging," *Magnetic Resonance Imaging*, Vol. 3, pp. 329–343, 1985, have presented an analytical treatment of the geometric distortion and the pixel intensity variation for objects such as cylinders and spheres. Pixel intensity variations due to susceptibility effects have been investigated by many others. Czervionke et al., "Magnetic Susceptibility Artifacts in Gradient-Recalled Echo MR Imaging," *American Journal of Neuro-Radiology*, November–December 1988, have performed a qualitative study of susceptibility induced misregistration. However, no one has carefully quantified the magnitude of the errors due to magnetic susceptibility. Table 1 presents the magnetic susceptibility of various materials.

TABLE 1

| For $B_0$ = 1.5 T, $G_z$ = 3.13 mT/m, FOV = 240 mm, 32 kHz, 256 pixels | | | | | | | |
|---|---|---|---|---|---|---|---|
| Material | Signal? | Z Mol. Wt. | $\chi z$ ppm mol$^{-1}$ | $\rho$ gcm$^{-3}$ | $\chi$ ppm cm$^{-3}$ | $\Delta z_i$ mm | $\Delta z_i$ pixels |
| $H_2O$ | Yes | 18 | −12.97 | 1.0 | −9.05 | 0.0 | 0.0 |
| Air | No | | 0.0 | | 0.0 | 2.15 | 2.29 |
| Ethanol ($C_2H_5OH$) | Yes | 46 | −33.6 | 0.79 | −7.25 | 0.43 | 0.46 |
| Ethonol + $H_2O$ 2:1 | Yes | | | | −7.79 | 0.3 | 0.32 |
| $Cu(SO)_4$ | Yes | 160 | 1330.0 | 3.6 | 377.0 | | |
| $Cu(SO)_4$ + $H_2O$ 0.12 g/ml | Yes | | | | 3.52 | 3.01 | 3.21 |
| Bone | No | | | 1.7–2.0 | −8.86 | 0.05 | 0.05 |
| Pyrex (Corning 7740) | No | | | 2.25 | −13.91 | −1.11 | −1.19 |

| X: | −13.91 | −9.05 | −8.86 | −7.79 | −7.25 | 0.0 | 3.52 | 377 |
|---|---|---|---|---|---|---|---|---|
| | Pyrex | $H_2O$ | Bone | Ethanol + $H_2O$ | Ethanol | Air | $Cu(SO)_4$ + $H_2O$ | $Cu(SO)_4$ |
| $\Delta z_i$ (mm) | −1.11 | 0.0 | 0.05 | 0.3 | 0.43 | 2.15 | 3.01 | |

The largest variation of the magnetic susceptibility, $\chi$, occurs at the boundary of tissue and air. Clinically important anatomic locations in the head where such interfaces occur include the pituitary gland, nasal cavities, the orbits and the mastoid bone. Similar variations in $\chi$ occur at many other important anatomic sites throughout the body. The boundaries of such structures can be distorted by as much as 2 mm for $B_o$=1.5 T, $G_z$=3.13 mT/m.

Figure 3:
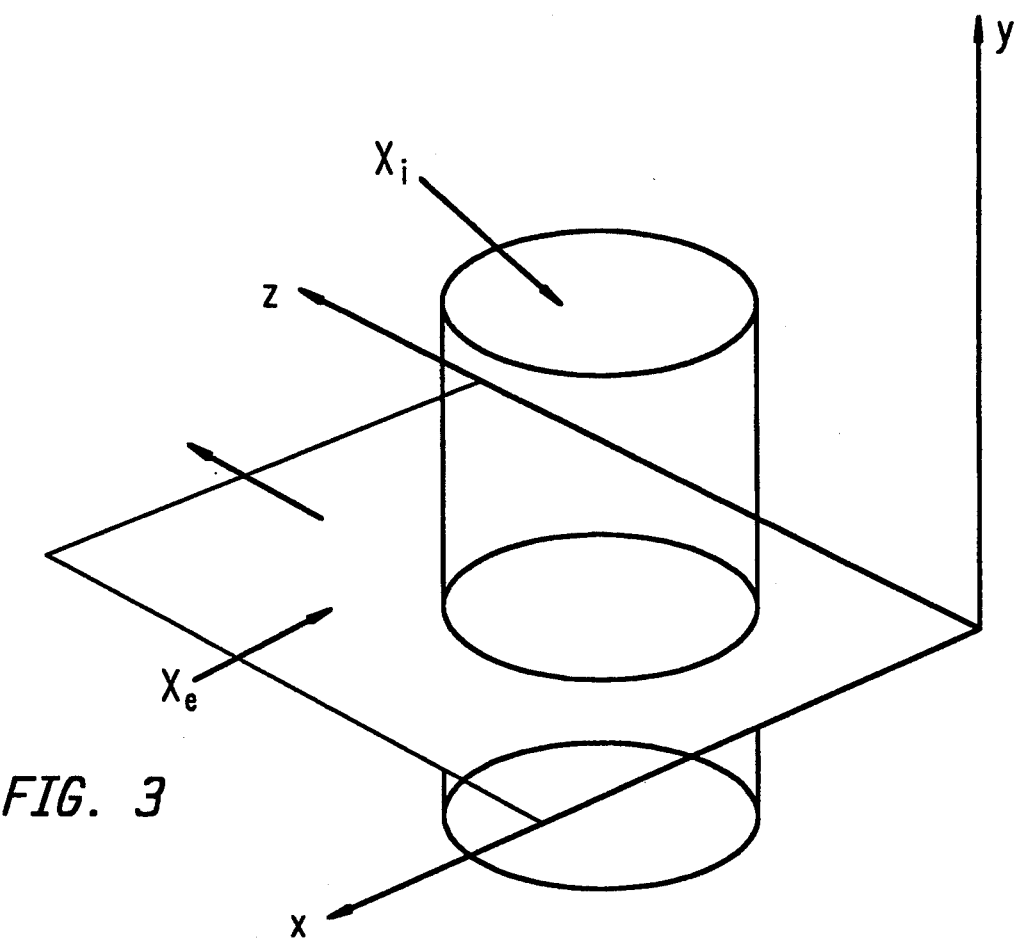
FIG. 3 illustrates a cylinder of radius R and magnetic susceptibility $\chi_i$ in a medium $\chi_e$.

Consider an infinitely long cylindrical object of radius R and magnetic susceptibility $\chi_i$ placed in a medium (as in FIG. 3) whose susceptibility is $\chi_e$, and scanned in the xz-plane, with z being the read-out direction. Lüdeke et al. supra, showed that in the MR image, the internal boundary of the cylinder shifts in the z direction (FIG. 4) by an amount given by:

$$\Delta z_i = \frac{\Delta \chi}{2} \frac{B_0}{G_z}, \tag{1}$$

where $\Delta\chi = \chi_i - \chi_e$. The external boundary shifts according to the formula:

$$\Delta z_e = \Delta z_i \frac{R^2 - 2x^2}{R^2}. \tag{2}$$

Note that when $x=0$, $\Delta z_e = \Delta z_i$; when $x=R/\sqrt{2}$ (i.e. at a point 45° from the x-axis on the boundary of the circle), $\Delta z_e = 0$ and when $x=R$, $\Delta z_e = \Delta z_i$. Thus the geometric distortion of a cylindrical object can be described analytically. $\Delta z_i$ in equation 1 can be used as a measure of magnetic susceptibility distortion.

Figure 5:
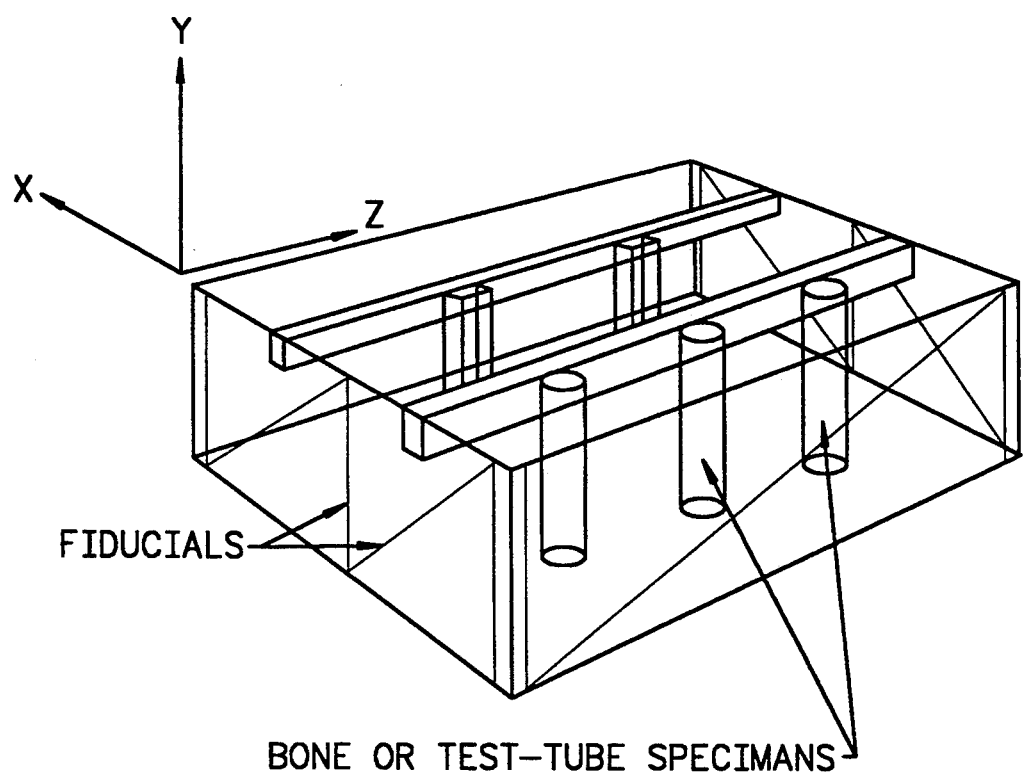
FIG. 5 illustrates a phantom used in measurements.

We have tested the amount of susceptibility distortion present at two different interfaces: bone/tissue and air/tissue. Machined cattle bone (femur) cylinder specimens and test-tubes were placed in water filled phantom shown in FIG. 5. This is a cubic tank made of plexiglass with fiducial markers. Tubes filled with Copper Sulfate solution and plexiglass straps served as fiducials. In the air/bone study, we placed 5 mm diameter and 60 mm long cylindrical bone specimens vertically in the water tank. For the second study we mounted test tubes with internal diameter ranging from 5.9 mm to 29.4 mm. The wall thickness for each of these tubes was about 1.0 mm.

For each study, the phantom was scanned using MR and CT. CT was used as a standard for comparison of the distortion. The Copper Sulfate fiducials were visible in MR images. The Plexiglass strap-fiducials were visible in CT images. The MR fiducials were detected by peak intensity detection in a small window around the fiducial. The CT fiducials were detected by edge detection followed by corner detection. A known Wang-Binford edge operator was used for detection. This edge operator has improved edge element position and orientation estimations over its prior art predecessor, the Canny's edge operator. Using the fiducials, translation, rotation and scaling between MR and CT spaces were found. We represented transformation using quaternions with only 9 parameters. Levenberg-Marquart non-linear optimation was used to estimate those 9 parameters. Once the transformation from CT to MR was known, for each MR plane, CT edges were projected onto that plane and compared with the MR edges. CT edges were assumed to be distortion free.

Figure 6:
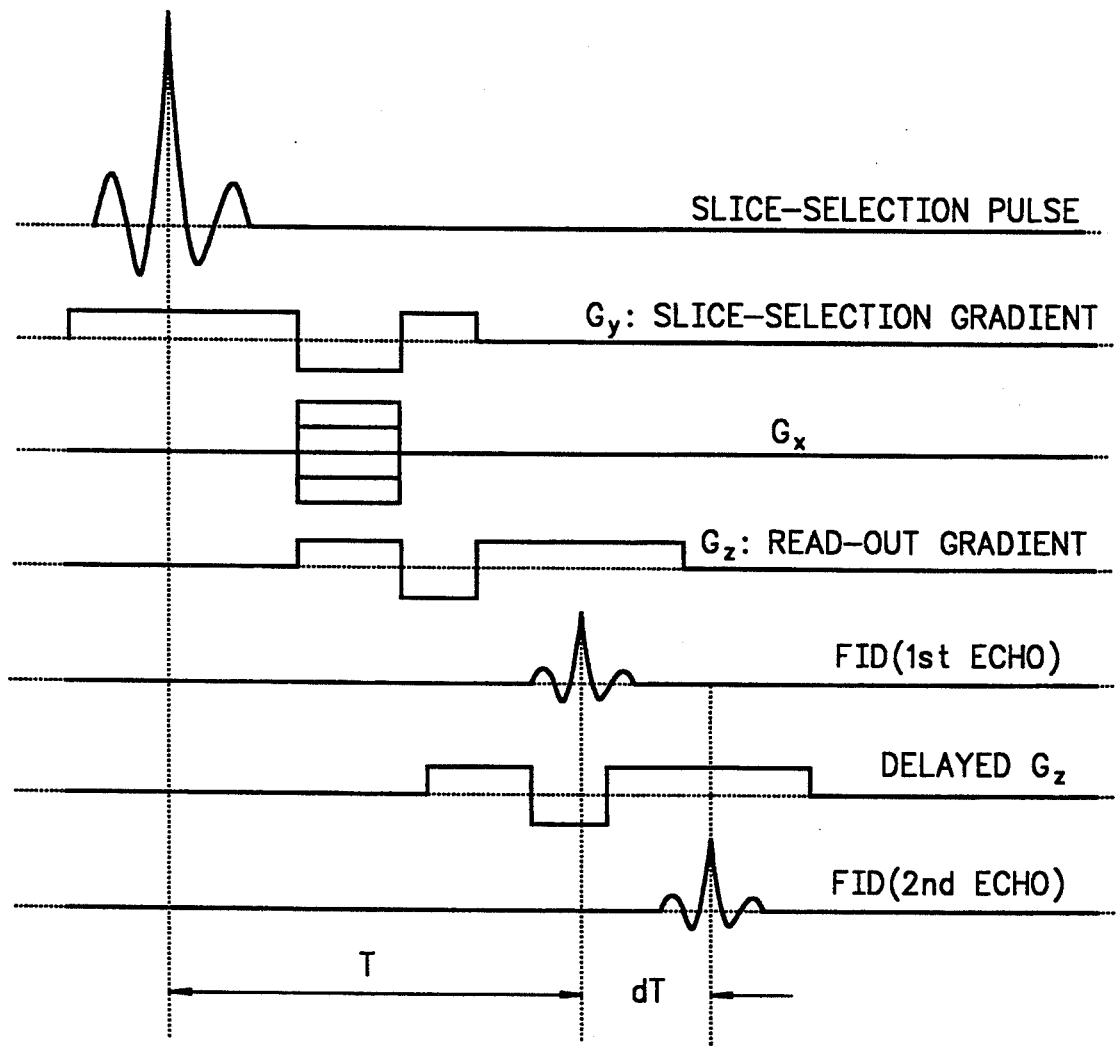
FIG. 6 illustrates a gradient recalled echo (GRE) sequence used for acquiring of $B_o$ map for the phantom of FIG. 5.

Schneider et al., "Rapid in-vivo Proton Shimming," *Magnetic Resonance in Medicine*, Vol. 18, pp. 335–347, 1991, have outlined a method for shimming the main magnet in Gradient Recalled Echo (GRE) MR imaging sequences. Our method to correct the geometric distortion is an extension and new application of this work. Let us consider the one dimensional case where we scan a line along the z-axis using a GRE sequence shown in FIG. 6. Let $\Omega(z)$ be the shift in frequency at the location z due to magnetic susceptibility variations. Schneider et al. showed that $\Omega(z)$ can be estimated by acquiring two scans at echo times T and $T+\Delta T$ with the following assumptions:

1. The human body has two major constituents which generate MR signals: water and lipid.
2. Misregistrations due to magnetic susceptibility variations and chemical shift are negligibly small.

The validity of the assumption 1 is well-known. For typical operating conditions, $G_z=3.13$ mT/m and $B_o=1.5$ T, the chemical shift is about 1.5 mm and the magnetic susceptibility distortion is less than about 2 mm (table 1). Hence the assumption 2 is also valid. Let the image intensity for echo time T be p(z,T) and the chemical shift between water and lipid be $\omega_f$ where z denotes vector location in the image. Choosing $\Delta T$ such that $\omega_f \Delta T = 2\pi$, it can be shown that:

$$\Omega(z) = \frac{\text{phase}\left\{\frac{p(z,T+\Delta T)}{p(z,T)}\right\}}{\Delta T} \quad (3)$$

Once the frequency shift $\Omega(z)$ is known, the registration error $\Delta z(z)$ in the image is obtained from the equation $$\gamma G_z \Delta z(z) = \Omega(z)$$

where $\gamma$ is the gyromagnetic ratio for the protons, and $G_z$ is the amplitude of the frequency encoding gradient employed during the imaging process. The result is a map $\Delta z(z)$ which defines, at each location z in the image, the deviation of the pixel from its true location. The final step is to correct the image by remapping it using new values of z as $$p^1(x,y,z) = p(x,y,z-\Delta z)$$

Based on equation 3 we can obtain a position-error profile for the pixels by performing two scans and calculating the phase difference between the two images. Knowing this error profile, we then shift the pixels in the image to their true locations. This followed by interpolation and resampling gives the corrected MR image. In practice however, the phase of $p(z,T+\Delta T)/p(z,T)$ could be more than $2\pi$. In this case, the phase wraps around. In order to unravel this wrapped phase, one can use a known phase unraveling method.

The invention has been verified experimentally. The cortical bone of a cattle femur was shaped into a small cylinder of 5 mm diameter and 10 mm in length. Using a SQUID (Superconducting Quantum Interference Device magnetometer), we measured the magnetic moment of this specimen at two temperatures with a magnetizing field of $10^4$G. Using the weight of the bone specimen (1.01 g) and the density of bone ([18]), 1.85 g.cm$^{-3}$, we calculated the magnetic susceptibility with respect to air. The results are shown in table 2. M and X are the magnetic moment and the magnetic susceptibility of the specimen respectively. $\sigma_M$ and $\sigma_\chi$ are the standard deviation of the error in the above measurements.

TABLE 2

| Temp. °K. | $M$ $10^{-3}$ emu | $\sigma_M$ $10^{-5}$ emu | $\chi$ ppm | $\sigma_\chi$ ppm |
| --- | --- | --- | --- | --- |
| 260 | −3.7353 | 6.1318 | −8.60 | 0.1412 |
| 300 | −3.8480 | 0.3424 | −8.86 | 0.0079 |

Equation (1) was used to quantify the amount of distortion present at various boundaries. For the bone/tissue interface the magnetic susceptibility distortion was smaller than the resolution of the MR images (0.9375 mm). This is not surprising since the magnetic susceptibility of bone is about the same as that for tissue (table 2). The distortion in this case is negligibly small.

Figure 4:
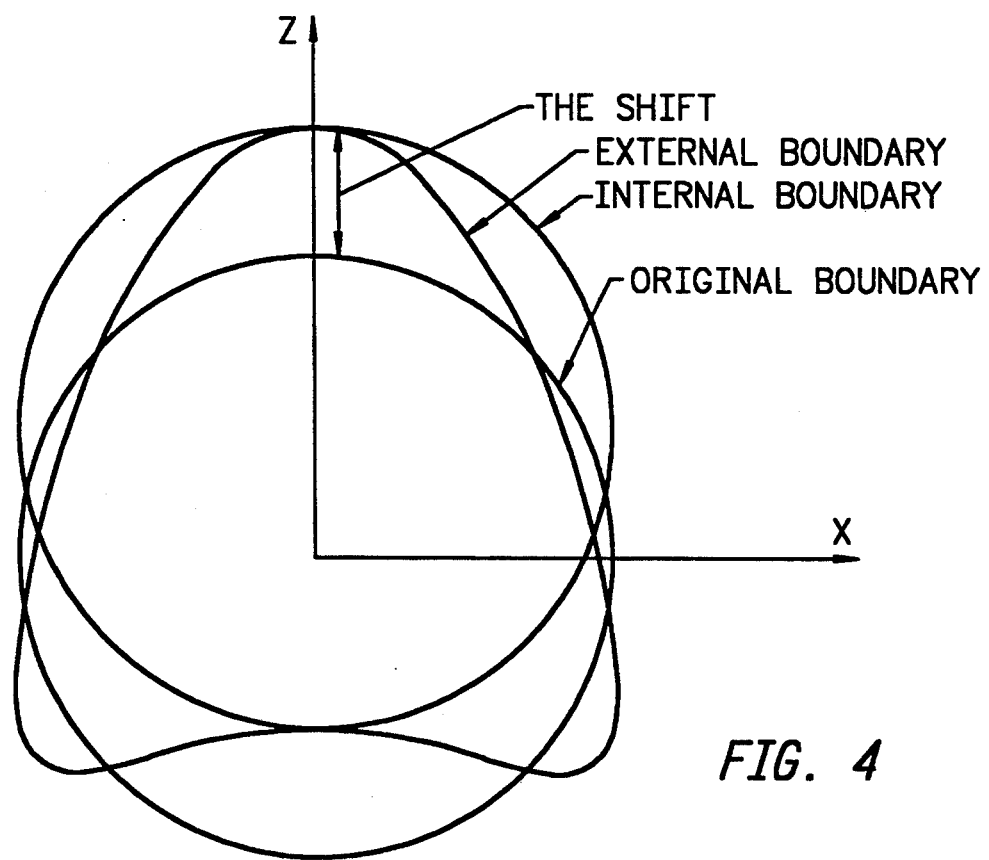
FIG. 4 illustrates the shifts of the internal and external boundaries of the cylinder of boundaries of the cylinder of FIG. 3 with read out in the z direction.
Figure 7B:
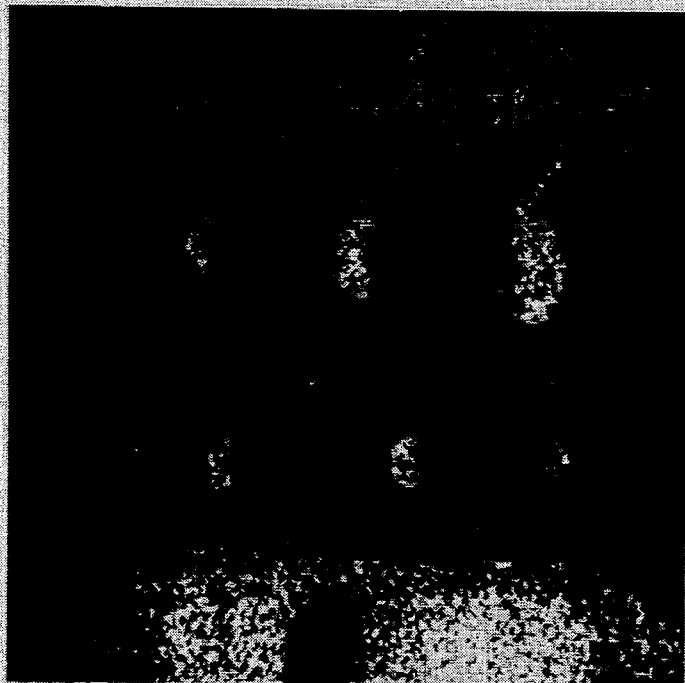
FIG. 7A and FIG. 7B are an MR image of the phantom of FIG. 5 with an air/water interface and the corresponding $B_o$ profile, respectively.
Figure 7A:
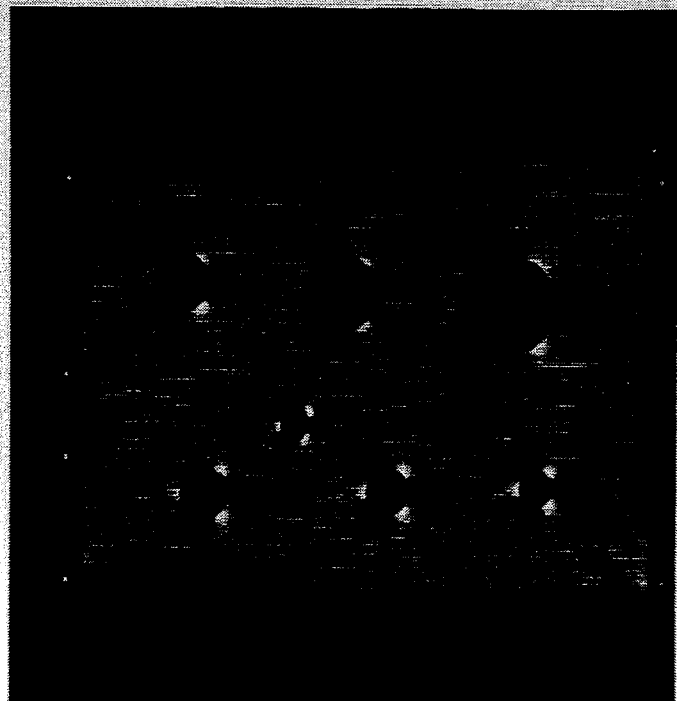
Figure 8B:
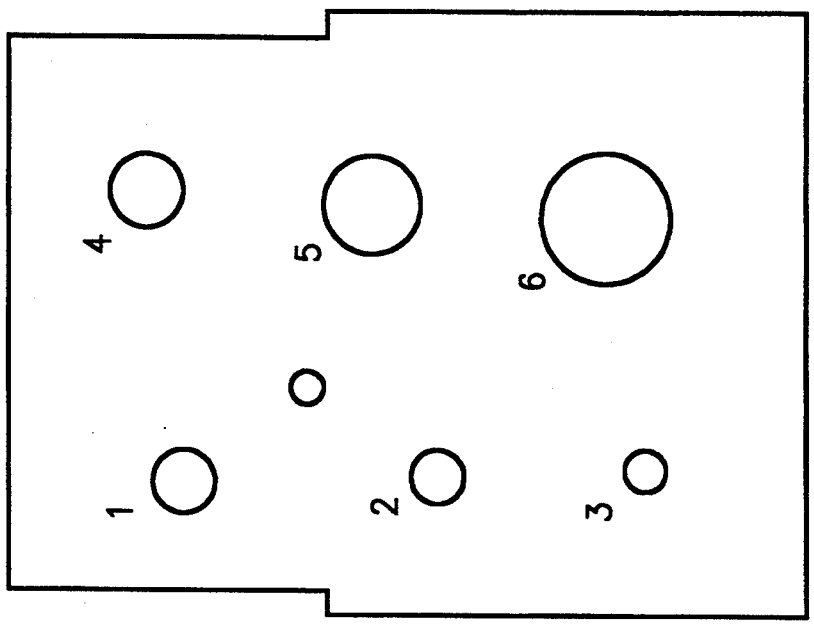
FIG. 8A and FIG. 8B are edges of an original MR image and the edges of a corrected MR image using the invention overlayed on the corresponding edges of a CT image, respectively.
Figure 8A:
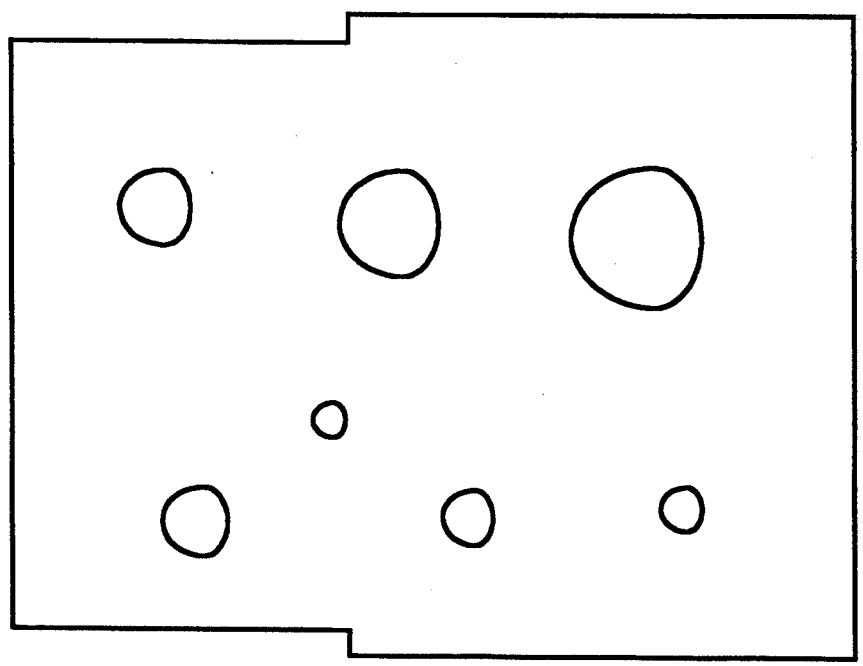

FIGS. 7A, 7B show some typical scans for the air/tissue interface. FIG. 7A is a MR scan of our phantom while FIG. 7B shows the corresponding error profile. Shown in FIG. 8A are the uncorrected edges of the MR plane in FIG. 7. Notice the similarity of the arrowhead shaped distortions of the circular cross-sections shown in FIG. 4. Corrected MR edges overlaid on the corresponding CT edges are shown in FIG. 8B. The arrowhead shape in FIG. 4 is expressed by the equation (see Lüdeke et al., supra):

$$z = \pm \sqrt{R^2 - x^2} + \Delta_\chi \frac{B_0}{2G_z} \frac{R^2 - 2x^2}{R^2}$$

The following table 3 demonstrates the disparity between CT images and corrected MR images:

TABLE 3

| Test-tube number | Center co-ord. (mm) Disparity | Std. dev. | Radius (mm) Disparity | Std. dev. |
| --- | --- | --- | --- | --- |
| 1 | (−0.13, 0.46) | (0.05, 0.19) | −0.20 | 0.55 |
| 2 | (0.02, 0.08) | (0.03, 0.23) | 0.08 | 0.21 |
| 3 | (0.16, 0.15) | (0.05, 0.26) | −0.55 | 0.76 |
| 4 | (−0.11, 0.53) | (0.04, 0.23) | −0.14 | 0.30 |
| 5 | (−0.06, 0.23) | (0.03, 0.23) | −0.18 | 0.20 |
| 6 | (−0.06, 0.34) | (0.05, 0.17) | −0.55 | 0.78 |

The parameter of the equation, $\chi$ can be fit to the arrowhead shapes detected in FIG. 8A by varying $\chi$. The susceptibility difference at the MR edges corresponds to the water/pyrex-glass boundary since pyrex glass test-tubes have been used. Table 4 summarizes susceptibility estimates at the water/pyrex-glass boundary before and after correction for the MR images:

TABLE 4

| | $\chi$ ppm | $\sigma_\chi$ ppm | $\Delta z_i$ mm | $\sigma_{\Delta zi}$ mm |
| --- | --- | --- | --- | --- |
| MR (before) | −4.12 | 1.01 | −0.99 | 0.24 |
| MR (after) | 0.15 | 0.63 | 0.03 | 0.15 |
| CT | 0.08 | 0.37 | 0.02 | 0.09 |

Susceptibility was also estimated from the CT edges for comparison. The corresponding geometric distortion was also calculated using equation 1 and is shown in table 3. The magnetic susceptibility of pyrex glass (Corning 7740) is −4.86 ppm with respect to water while from the table 3, our estimate is −4.12 ppm with a standard error of 1.01 ppm. Also our algorithm was able to correct the distortion of the MR images from 0.99 mm to 0.03 mm. The theoretically estimated geometric distortion at the air/tissue boundary is 2.15 mm (see table 1).

Figure 9A:
FIG. 9A and FIG. 9B are a head scan MR image and the distortion error profile, respectively.
Figure 9B:
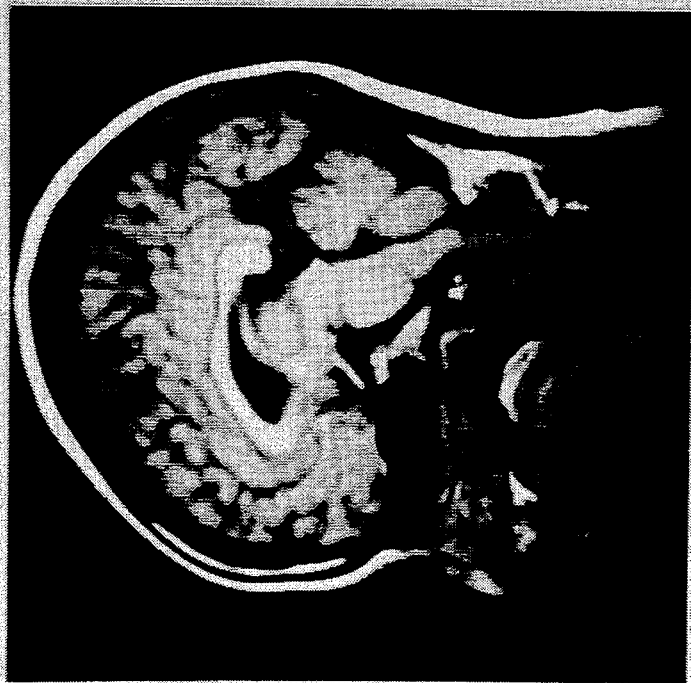
Figure 10:
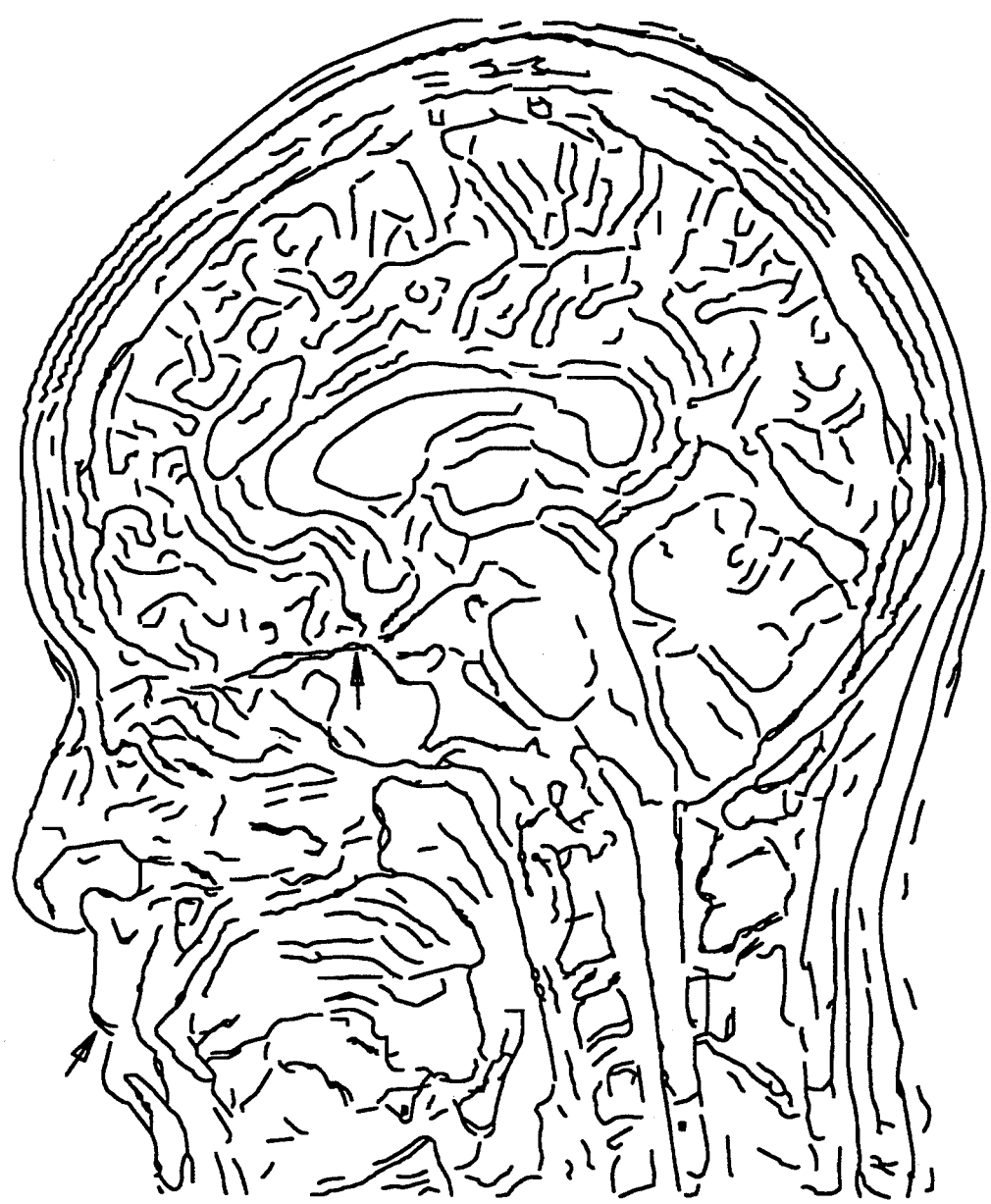
FIG. 10 illustrates corrected MR edges overlaid on uncorrected edges in the head scan MR image of FIG. 9A with shifts noted by arrows.

FIGS. 9A, 9B show a head scan and its error profile. The corrected edges (thick) of the head are overlaid on the uncorrected edges (thin) in FIG. 10. Brain area has only a slight magnetic susceptibility variation. The largest magnetic susceptibility changes occur at the sinus cavity and at the skin. Notice that shifts have taken place in opposite directions at the boundaries marked with arrows. Shifts occurred along the vertical read-out direction.

We have disclosed a method and apparatus for correcting the most complex geometric distortion in MR which occurs due to the magnetic susceptibility variations in the imaging volume. We have demonstrated that the MR geometric distortion at the tissue/bone interface due to magnetic susceptibility variations is negligibly small while that at the air/tissue boundary can be 2 mm or more. We have shown that the new in-vivo method corrects the distortion due to magnetic susceptibility variations and that this method was able to reduce the distortion at water/pyrex-glass boundary from 0.99 mm down to 0.03 mm.

Although the pulse sequence presented here was a GRE sequence, the geometric distortion due to magnetic susceptibility variations occurs in the case of any pulse sequence. Spin-echo sequences which in general do not give rise to any signal amplitude distortion due to magnetic susceptibility variations, may also suffer from the geometric distortion. The geometric distortion correction method presented here can be extended to any pulse sequence chosen for a particular image contrast, provided that a $B_0$ map is acquired separately. A $B_0$ map can be obtained with little time penalty by using a rapid GRE sequence as disclosed herein or by using a spin echo sequence. Alternatively, the $B_0$ map can also be acquired by using two echoes after a single excitation. In the spin echo sequence at least two different sequences must be employed with, for example, the 180° phase inversion pulses occurring at different times following the 90° flip pulses.

Thus, it is possible to extract geometric information from MR images with high accuracy. As demonstrated, magnetic susceptibility of materials can be measured from the images provided their shapes in the images can be described mathematically as in the case of cylinders. While the invention has been described with reference to a specific embodiment, the description is illustrative of the invention and is not to be construed as limiting the invention. Various modifications and applications may occur to those skilled in the art without departing from the true spirit and scope of the invention as defined by the appended claims.

Attached hereto and incorporated by reference is a paper co-authored by Thilaka S. Sumanaweera, Gary H. Glover, and John R. Adler, applicants herein, along with Thomas O. Binford entitled "MR Susceptibility Distortion Quantification and Correction for Stereotaxy" which will be published in the Proceedings of the SPIE/SPSE Symposium on Electronic Imaging, Section on Biomedical Image Processing III and 3-D Microscopy, February 9–14, 1992 at San Jose, Calif. The paper discusses the invention described and claimed herein and provides additional prior art.

What is claimed is:

1. A method of correcting spatial distortion in magnetic resonance images due to magnetic field inhomogeneity including inhomogeneity due to susceptibility variations in an object being imaged comprising the steps of
    a) placing the object in a magnetic field ($B_0$) oriented along an axis in a three axis coordinate system;
    b) applying first RF pulses to said object and a magnetic gradient along a first axis;
    c) applying first magnetic gradients along at least one axis in a plurality of first read-out of sequences,
    d) detecting a plurality of magnetic resonance signals in response to said plurality of first read-out sequences;
    e) processing said plurality of magnetic resonance signals to obtain a first complex image in an image plane;
    f) repeating steps b) through e) for second RF pulses, second magnetic gradients, and second read-out sequences and obtaining a second complex image in said image plane;
    g) obtaining a position-error profile for pixels from said complex images; and
    h) remapping the locations of pixels in the image plane using said position-error profile of said pixels.

2. The method as defined by claim 1 wherein said read-out sequences are spin echo sequences and include 180° phase inversion pulses following 90° phase excitation pulses with the 180° pulses occurring at different times following the 90° pulses.

3. The method as defined by claim 1 wherein step c) and f) include applying at least two gradient-recalled echo sequences having echoes at different times.

4. The method as defined by claim 3 wherein step (g) includes obtaining registration error $\Delta z(z)$ from $$\gamma G_z \Delta z(z) = \Omega(z)$$

where $\gamma$ is the gyromagnetic ratio for protons, $G_z$ is a magnetic gradient along a Z axis and $\Omega(z)$ is frequency shift at the location, z, due to magnetic field inhomogeneity including inhomogeneity due to magnetic susceptibility variations defined as $$\Omega(z) = \frac{\text{phase}\left(\frac{p(z,T+\Delta T)}{p(z,T)}\right)}{\Delta T}$$

where $p(z,T+\Delta T)$ is the image intensity for echo at time $T+\Delta T$, $p(z, T)$ is the image intensity for echo at time T, $\Delta T = 2\pi/\omega_f$, and $\omega_f$ is the chemical shift between water and lipid.

5. The method as defined by claim 3 wherein step (h) includes remapping the image using new values of z from $$p'(x,y,z) = p(x,y,z-\Delta z)$$

where p' = new image intensity and p = old image intensity.

6. Apparatus for use in correcting spatial distortion in magnetic resonance images due to magnetic field inhomogeneity including inhomogeneity due to susceptibility variations in a object being imaged comprising
   a) means for establishing a magnetic field ($B_0$) through said object along an axis in a three axis coordinate system;
   b) means for applying first RF pulses to said object and a first magnetic gradient along a first axis;
   c) means for applying first magnetic gradients along at least one axis in a plurality of first read-out sequences,
   d) means for detecting a plurality of magnetic resonance signals in response to said plurality of first read-out sequences;
   e) means for processing said plurality of first magnetic resonance signals to obtain a first complex image in an image plane;
   f) means for applying second RF pulses to said object and a second magnetic gradient along said first axis;
   g) means for applying second magnetic gradients along said at least one axis in a plurality of second read-out sequences;
   h) means for detecting a plurality of second magnetic resonance signals in response to said plurality of second read-out sequences;
   i) means for processing said plurality of second magnetic resonance signals to obtain a second complex image in said image plane;
   j) means for obtaining a position-error profile for pixels from said complex images; and
   k) means for shifting the location of pixels in the image plane using said position-error profile of said pixels.

7. Apparatus as defined by claim 6 wherein said read-out sequences are spin echo sequences and include 180° phase inversion pulses following 90° phase pulses with the 180° pulses occurring at different times following the 90° pulses.

8. Apparatus as defined by claim 6 wherein said read-out sequences are gradient-recalled echo sequences having echoes at different times.

9. Apparatus as defined by claim 7 wherein said means for obtaining a position error profile includes means for obtaining registration error $\Delta z(z)$ from $$\gamma G_z \Delta z(z) = \Omega(z)$$

where $\gamma$ is the gyromagnetic ratio for protons, $G_z$ is a magnetic gradient along a Z axis and $\Omega(z)$ is frequency shift at the location, z, due to magnetic field inhomogeneity including inhomogeneity due to magnetic susceptibility variations and defined as $$\Omega(z) = \frac{\text{phase}\left(\frac{p(z,T+\Delta T)}{p(z,T)}\right)}{\Delta T}$$

where $p(z,T+\Delta T)$ is the image intensity for echo time $T+\Delta T$, $p(z,T)$ is the image intensity for echo time T, $\Delta T = 2\pi/\omega_f$, and $\omega_f$ is the chemical shift between water and lipid.

10. Apparatus as defined by claim 8 wherein said means for shifting the location of pixels includes means for remapping the image using new values of z from $$p'(x,y,z) = p(x,y,z-\Delta z).$$

where p' = new image intensity and p = old image intensity.

* * * * *